United States Patent
Jakubowska et al.

(10) Patent No.: US 9,354,201 B2
(45) Date of Patent: May 31, 2016

(54) ION MOBILITY SPECTROMETER CHAMBER

(75) Inventors: Malgorzata Jakubowska, Warsaw (PL); Wiestaw Gallewicz, Warsaw-Wesola (PL); Michal Ceremuga, Wielgolas Brzezinski (PL); Miroslaw Maziejuk, Zabki (PL)

(73) Assignee: WOJSKOWY INSTYTUT CHEMII I RADIOMETRII, Warszawa (PL)

( * ) Notice: Subject to any disclaimer, the term of this patent is extended or adjusted under 35 U.S.C. 154(b) by 0 days.

(21) Appl. No.: 14/117,627

(22) PCT Filed: May 16, 2012

(86) PCT No.: PCT/PL2012/000033
§ 371 (c)(1),
(2), (4) Date: Oct. 19, 2015

(87) PCT Pub. No.: WO2012/158052
PCT Pub. Date: Nov. 22, 2012

(65) Prior Publication Data
US 2016/0069836 A1    Mar. 10, 2016

(30) Foreign Application Priority Data
May 17, 2011  (PL) ......................................... 394898

(51) Int. Cl.
*H01J 49/00* (2006.01)
*G01N 27/62* (2006.01)

(52) U.S. Cl.
CPC .................................. *G01N 27/624* (2013.01)

(58) Field of Classification Search
CPC .. G01N 27/624; G01N 27/622; H01J 49/0018
USPC .......................... 250/281, 282, 288, 290, 292
See application file for complete search history.

(56) References Cited

U.S. PATENT DOCUMENTS

| | | | |
|---|---|---|---|
| 7,098,449 B1 * | 8/2006 | Miller ................. | H01J 49/0018 250/281 |
| 2002/0053637 A1 * | 5/2002 | Conn .................... | A61B 5/1486 250/281 |
| 2005/0133716 A1 * | 6/2005 | Miller ................. | G01N 27/624 250/293 |
| 2006/0214580 A1 * | 9/2006 | Bunker ................ | G01N 27/622 313/542 |

* cited by examiner

*Primary Examiner* — Michael Maskell
(74) *Attorney, Agent, or Firm* — John Alumit

(57) ABSTRACT

A FAIMS ion mobility spectrometer chamber with a high repeatability of dimensions, permitting stable gas flow, mechanical rigidity, excellent thermal conductivity, and high temperature stability of gas flow. The heating resistor, ionizer electrodes, HV detector electrodes and collecting electrodes, and conducting contacts, are applied in the form of layers of precious metals on ceramic plates. The heating resistor is located on the outer surface of the top and bottom ceramic plate in the form of a resistive layer of ruthenium dioxide. On the inner surface of each of the top and bottom ceramic plates, there are gas ionizer electrodes in the form of a layer of radioactive nickel, HV electrodes and collecting electrodes, in the form of layers of gold. The conducting contacts are made of a palladium-silver layer, whereas on the edge surfaces of the ceramic plates there are edge contacts, which are made of silver paste.

1 Claim, 2 Drawing Sheets

ION MOBILITY SPECTROMETER CHAMBER

CROSS-REFERENCE TO RELATED APPLICATION

Figure 1:
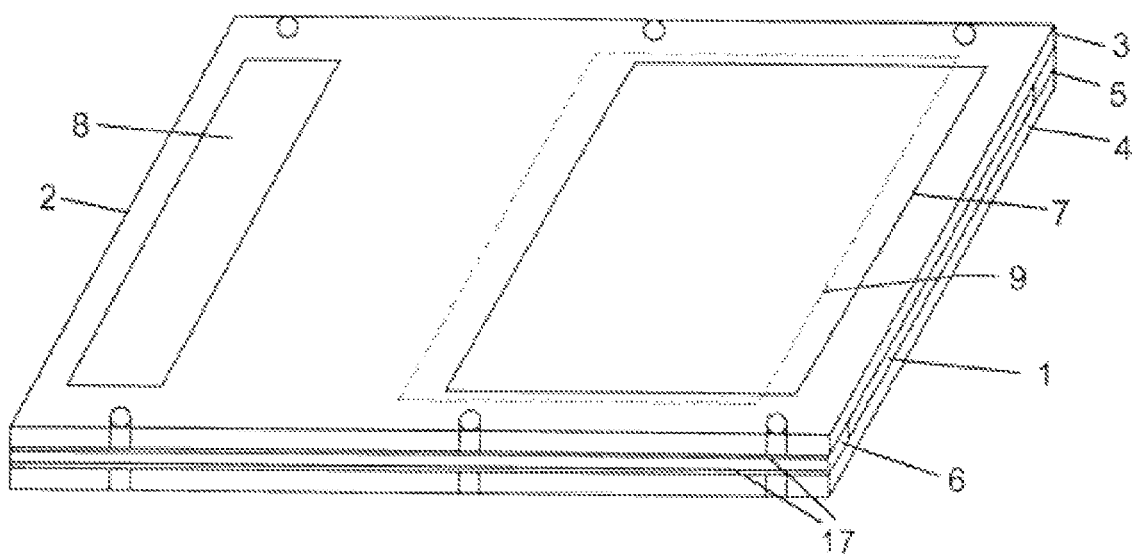

This application claims the benefit of the priority filing date of PCT application no. PCT/PL2012/000033 filed on May 16, 2012 and published in WO 2012/158052 on Nov. 22, 2012. The earliest priority filing date claimed is May 17, 2011.

FEDERALLY SPONSORED RESEARCH

Not Applicable

SEQUENCE LISTING OR PROGRAM

Not Applicable

BACKGROUND

This invention relates to a FAIMS (Field Asymmetric Ion Mobility Spectrometry) spectrometer chamber, a device intended to detect chemical contamination.

Modern spectrometer scanners detect and identify most organic substances regarded as highly toxic. Currently, the detection of highly toxic chemicals (chemical weapons and toxic industrial materials) is performed by detectors based on IMS technology (ion mobility spectrometry). These are typically classical spectrometers operating at a temperature of about 50° C., with high sensitivity, but not very high resolution, which in practice leads to false alarms. The indicator, after detecting chemical contamination, generates a warning signal, i.e. it activates a beep and light or sends a signal to activate user-defined devices, such as ventilation devices or alarm systems. The number of false alarms should be as low as possible, as this undermines confidence in the contamination detection system and may cause the unnecessary implementation of emergency procedures.

The IMS detector chamber is divided into two areas. The first is the area from the semi-permeable membrane to the injection grid, in which ionization takes place by a β- or α-radioactive source, the second is the drift area—from the injection grid to the collecting electrode. A high voltage (generally 1.5 kV to 3 kV) is applied to the grid in front of the radioactive source, while the metal rings from the source to the collecting electrode have ever lower potentials. The field is thus shaped so that the ions from the ionization area move in straight lines to the collecting electrode. Most gaseous substances have different rates of mobility, so the transit time of the ions through the drift area varies, allowing for their identification.

Currently there is much research being carried out into the improvement of the properties of devices used to detect contamination. One solution is the coupling of the classical ion mobility spectrometer with a spectrometer with a high intensity, high frequency transverse field—FAIMS in a cascade sequence. FAIMS technology is based on the phenomenon of the segregation of ions passing through the detector. The FAIMS detector is constructed of ceramic plates opposite each other to which high voltage is applied at high frequencies. Under the influence of the electric field created within the detector segregation takes place at the collecting electrode. The observed segregation of ions in the gas flowing through results from their varying mobility in fields of greater and lesser intensity. The mobility of the ions is dependent on mass, the charge of the ion and the velocity of the gas flow. Under the influence of an alternating electric field applied to the electrodes, ions whose mobility does not fulfill the conditions of stable flow through the detector are captured. Considering the dependence of the mobility of the ions from the particles migrating through the active interior of the spectrometer on the value of the compensated field, we are dealing with a type of ion filter. The structure of the hybrid FAIMS-IMS system is based on using the FAIMS spectrometer as the first step, but without the collecting electrode. It works on a principle similar to an ion trap. After passing through the ionization source, ions of the analyzed gas pass in to the ion trap, formed of two rectangular plates parallel to one another. Between the covers a high intensity field of over 10,000 [V/m] is applied. Thanks to the fact that the mobility of the ions is dependent on the electric field, ion separation can be achieved, since the electric field in the ion trap can be shaped such that only selected ions reach the collecting electrode.

FAIMS spectrometers are approximately 10 times as sensitive, furthermore, they permit the separation of gaseous substances such as acetone, benzene and toluene, which to date have not been differentiated by classical IMS spectrometers, even those with high resolution.

An important factor in the operating of FAIMS spectrometers, omitted in scientific reports or patent descriptions, is the temperature stability of the gas flow. The temperature of the gas has a significant effect on the mobility of the ions, thus it has an effect on the location of the electrical peaks arising from different gaseous substances.

The construction of such closed chambers in glass systems is known, allowing for high purity in the chamber, but unfortunately such systems do not ensure the appropriate temperature stability of the gas flow.

The aim of the invention was to develop a chamber in which the drawbacks of current devices have been eliminated.

SUMMARY

The essence of the FAIMS ion mobility spectrometer chamber in this invention, comprising an inlet and outlet for the analyzed gas, heating resistors, a gas flow ionizer, FAIMS detector and ionic current collecting electrodes, where the FAIMS detector comprises two electrodes separated by a gap, to which a high voltage high frequency current is connected, is that the heating resistors, the ionizer electrodes, the detector electrodes and the collecting electrodes, as well as the conducting contacts, are applied in the form of layers of precious metals on ceramic plates. The heating resistors are located on the outer surface of the ceramic plates, in the form of a resistive layer of ruthenium dioxide. On the inner surfaces of the top and bottom ceramic plate, sequentially, starting from the inlet of the gas into the chamber, there are gas ionizer electrodes in the form of layers of radioactive nickel, HV and collecting electrodes in the form of layers of gold. The conducting contacts are made of a palladium-silver layer. On the side edges of the ceramic plates there are edge contacts that are made of layers of silver.

Such a chamber has high repeatability of dimensions, permitting stable gas flow, mechanical rigidity, excellent thermal conductivity and high temperature stability of gas flow, resulting in the analyzed gas being of the same temperature throughout the chamber and the ability to produce a very strong electric field inside. The use of layers of precious metals on the electrodes and detection surfaces fully protects the instrument from corrosion and enables long-term, stable operation, without any changes in parameters.

DRAWINGS

Figure 2:
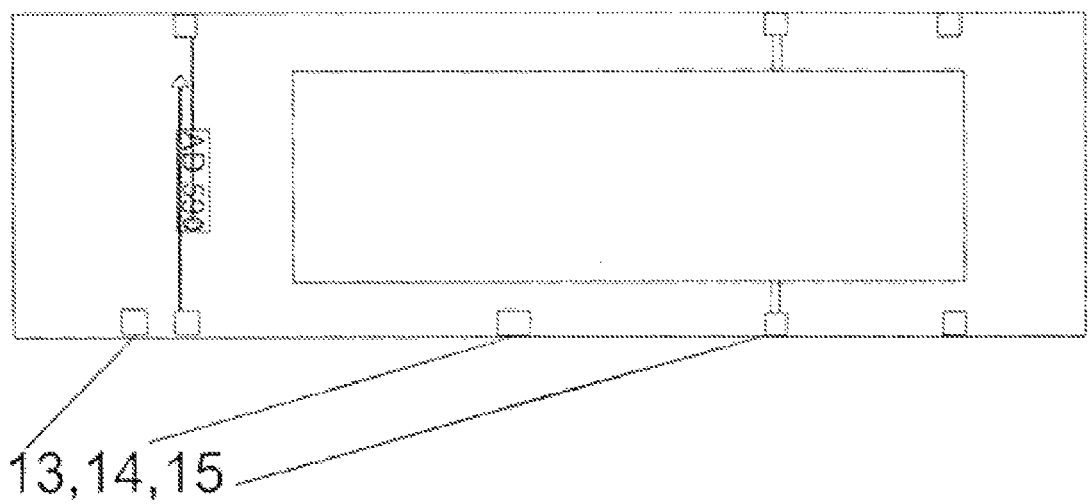
Figure 3:
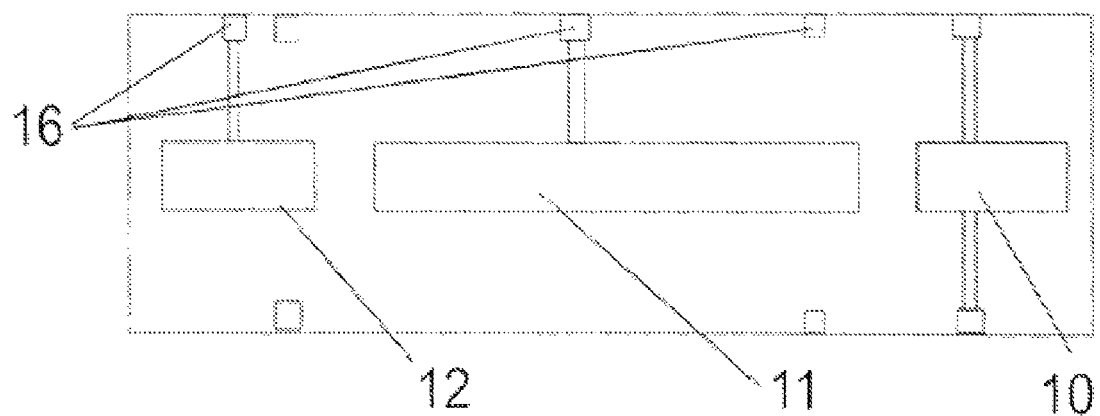

The chamber is shown in an example of the realization of this invention in the drawings where FIG. 1 shows a perspective view of the chamber,
FIG. 2—a view of the outer surface of the top plate, and
FIG. 3—a view of the inner surface of the top plate, identical to the view of the inner surface of the bottom plate.

DETAILED DESCRIPTION

The spectrometer chamber with the inlet 1 and outlet 2 of the analyzed gas is constructed from four ceramic plates, the top plate 3, the bottom plate 4 and two interstitial plates 5 and 6, ensuring the air-tightness of the chamber and a constant distance between the top and bottom plates. The ceramic plates are made of 96% $Al_2O_3$ alumina. The top and bottom plates have a thickness of 1/40", and the interstitial plates −1/100". On the outer surface of each of the top 3 and bottom 4 ceramic plates, there is a heating resistor 7 and temperature sensor 8. The heating resistor 7 constitutes a resistive layer of ruthenium dioxide paste, applied onto the ceramic plate. Above the resistor there is an electronic plate with an amplifier 9.

On each of the top 3 and bottom 4 ceramic plates on their inner surfaces there are, sequentially, starting from the gas inlet: ionizer electrodes 10, HV electrodes 11 and collecting electrodes 12. The ionizer electrode, in the form of a layer of radioactive Ni 63, is applied on a base of gold paste applied to the ceramic plate. Both the HV electrodes and the collecting electrodes are made of gold past. The conducting contacts 13, 14 and 15 are made of palladium-silver paste and the edge contacts 16 are made of silver paste.

After applying the above features onto the top plate 3 and the bottom plate 4, the two plates are bonded together with the interstitial plates 5 and 6 with low-melting sealing glass 17 at a temperature of 560° to 620° at a pressure of 8N to 12N, obtaining a monolithic, sealed chamber of a shape in accordance with the assumptions.

What is claimed:

1. A ion mobility spectrometer chamber, FAIMS type, with an inlet and outlet for the analyzed gas, a heating resistor, an ionizer of the gas flowing through, a FAIMS detector and electrodes collecting ionic current, where the FAIMS detector comprises two electrodes separated by a gap, to which a high voltage, high frequency current is connected, characterized in that the heating resistor (7), the ionizer electrodes (10), the HV detector electrodes (11) and the collecting electrodes (12), as well as the conducting contacts (13,14,15), are applied in the form of layers of precious metals on ceramic plates (3,4), where the heating resistor (7) is located on the outer surface of the top (3) and bottom (4) ceramic plate in the form of a resistive layer of ruthenium dioxide, on the inner surface of each of the top (3) and bottom (4) ceramic plates, sequentially, starting from the gas inlet (1) to the chamber, there are gas ionizer electrodes (10) in the form of a layer of radioactive nickel, HV electrodes (11) and collecting electrodes (12) in the form of layers of gold, and the conducting contacts (13,14,15) are made of a palladium-silver layer, whereas on the edge surfaces of the ceramic plates there are edge contacts (16), which are made of silver layer.

* * * * *